(12) United States Patent
Brain

(10) Patent No.: US 8,449,713 B2
(45) Date of Patent: May 28, 2013

(54) GASTRO-LARYNGEAL MASK

(75) Inventor: Archibald I. J. Brain, Victoria (SC)

(73) Assignee: The Laryngeal Mask Company Limited, Victoria, Mahe (SC)

( * ) Notice: Subject to any disclaimer, the term of this patent is extended or adjusted under 35 U.S.C. 154(b) by 112 days.

(21) Appl. No.: 12/896,573

(22) Filed: Oct. 1, 2010

(65) Prior Publication Data

US 2011/0017388 A1    Jan. 27, 2011

Related U.S. Application Data

(60) Division of application No. 11/958,946, filed on Dec. 18, 2007, now abandoned, which is a continuation of application No. 09/803,452, filed on Mar. 8, 2001, now Pat. No. Re. 39,938, which is an application for the reissue of Pat. No. 5,878,745, which is a continuation of application No. 08/609,521, filed on Mar. 1, 1996, now abandoned.

(51) Int. Cl.
*B29C 69/00*       (2006.01)
*B29C 65/00*       (2006.01)
*B29C 45/00*       (2006.01)
*B65H 81/00*       (2006.01)
*B31B 1/60*        (2006.01)
*B32B 37/00*       (2006.01)
*B29D 30/00*       (2006.01)
*B29D 30/26*       (2006.01)
*A61M 15/00*       (2006.01)
*A61M 16/00*       (2006.01)
*A62B 9/06*        (2006.01)
*A62B 18/02*       (2006.01)
*A62B 18/08*       (2006.01)
*A62B 7/00*        (2006.01)

(52) U.S. Cl.
USPC ............. 156/293; 156/60; 264/295; 264/501; 128/200.24; 128/207.14; 128/207.15; 128/200.26; 128/206.21; 128/206.22; 128/204.18

(58) Field of Classification Search
USPC ........ 156/60, 293; 264/295, 501; 128/200.24, 128/200.26, 204.18, 206.21, 206.22, 207.14, 128/207.15
See application file for complete search history.

(56) References Cited

U.S. PATENT DOCUMENTS 5,249,571 A * 10/1993 Brain ....................... 128/207.14
5,305,743 A *  4/1994 Brain ....................... 128/207.15

* cited by examiner

*Primary Examiner* — Christopher Schatz
*Assistant Examiner* — Matthew Hoover
(74) *Attorney, Agent, or Firm* — Wilmer Cutler Pickering Hale and Dorr LLP

(57) ABSTRACT

A method of making a device by integrally molding. The device includes an inflatable mask comprising a relatively stiff component and a relatively soft compliant flexible component. The mask is insertable, at least when deflated, through a mouth of the patient to an inserted location within a patient. The inserted location is near a laryngeal inlet of the patient. The device also includes an airway tube and an evacuation tube coupled to the mask. The relatively soft compliant flexible component of the mask is integrally formed in a single moulding operation.

9 Claims, 3 Drawing Sheets

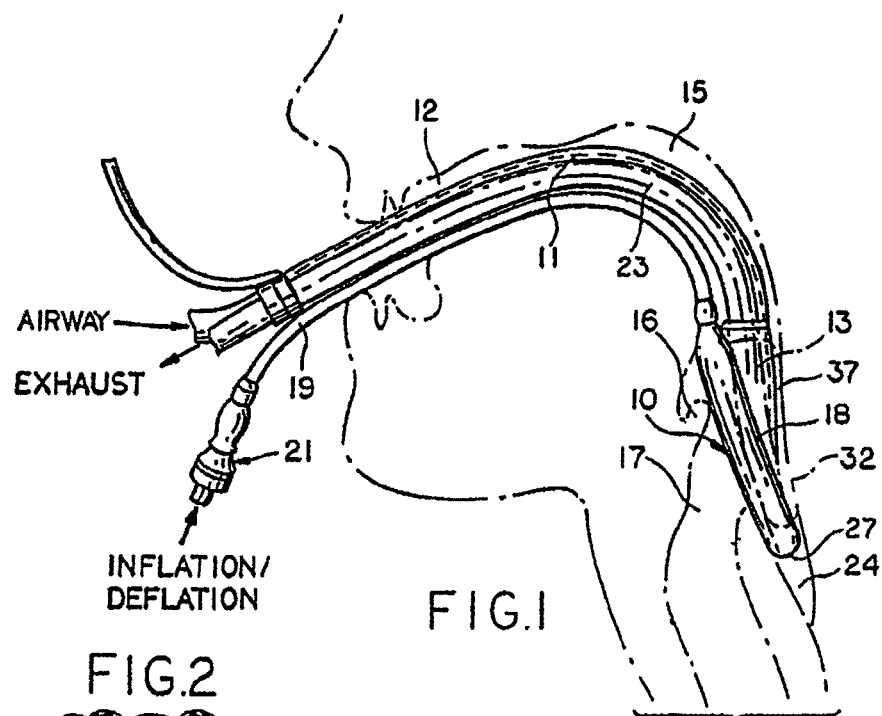
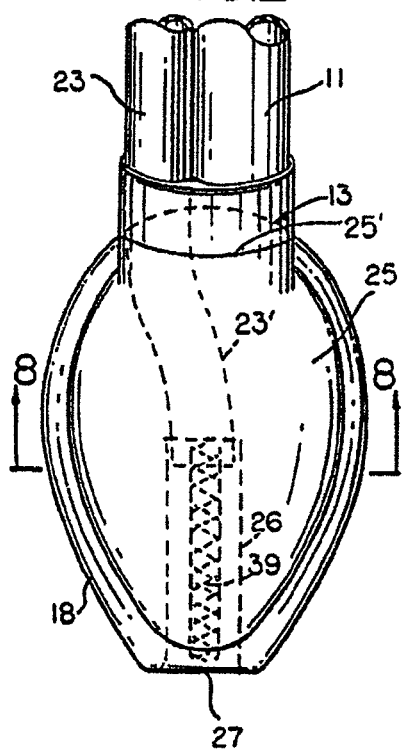
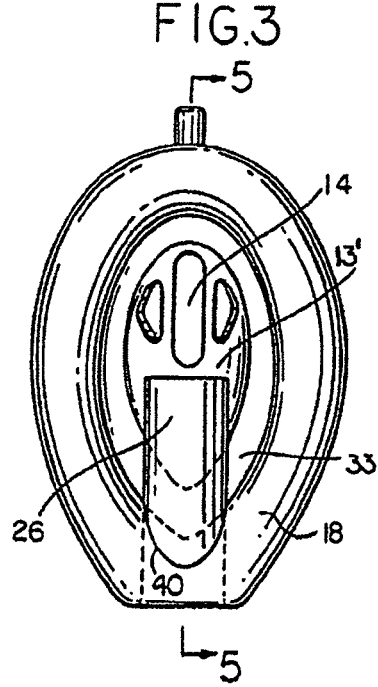
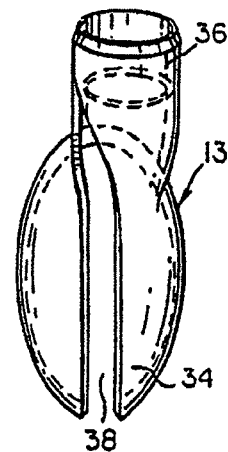
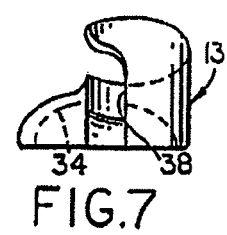

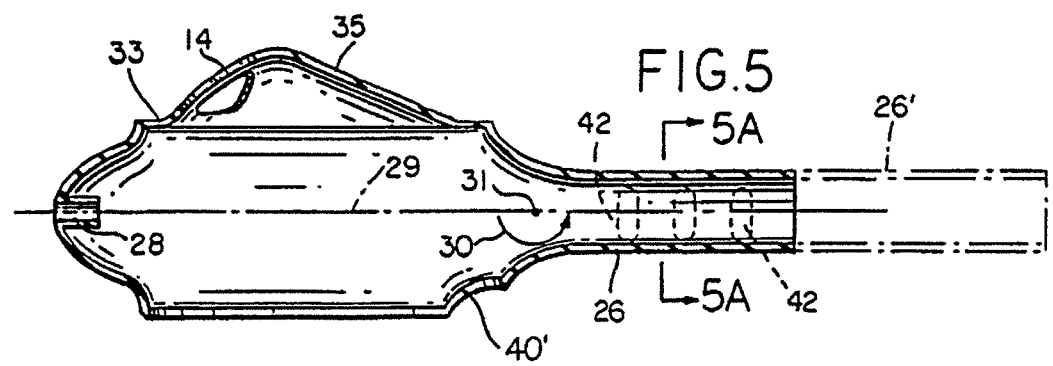
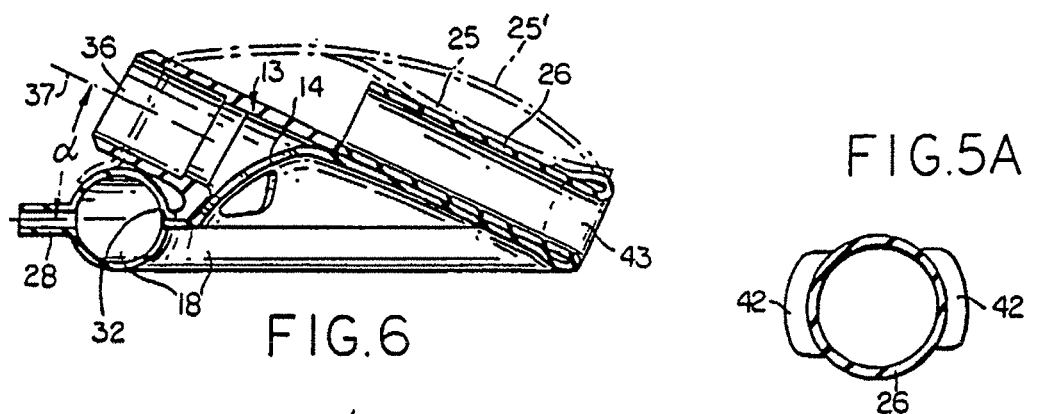
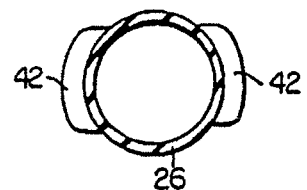
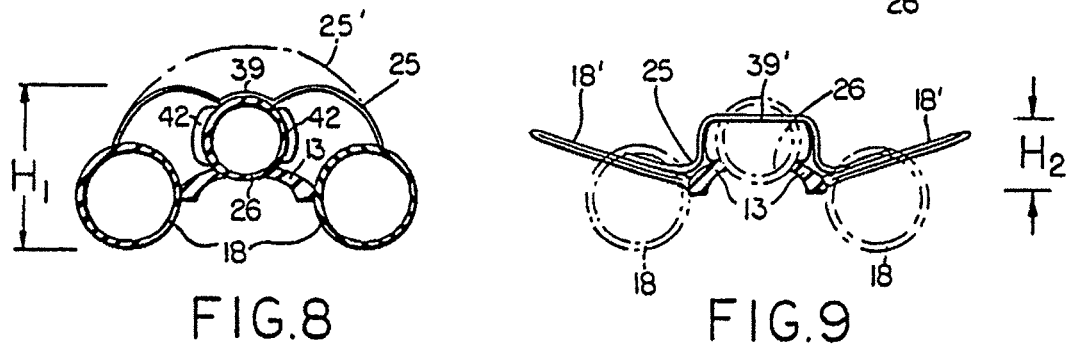

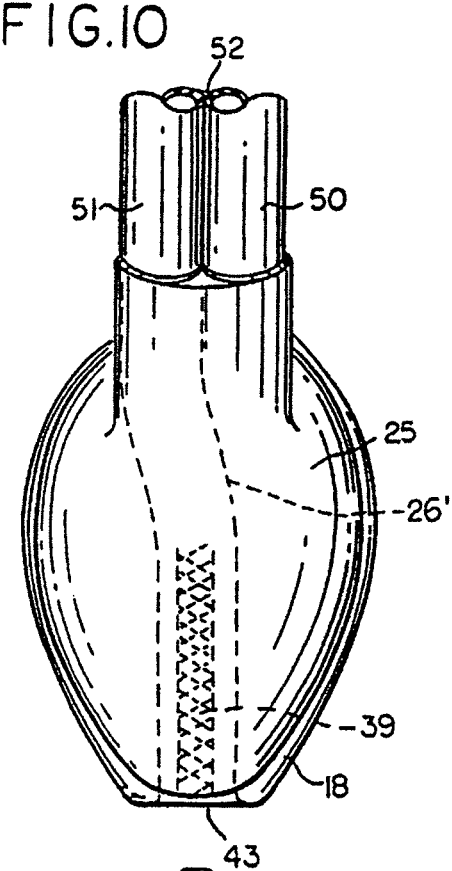
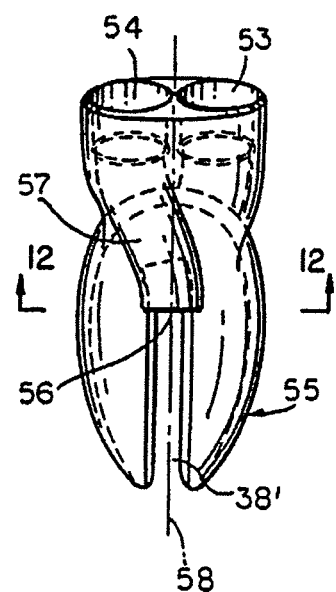
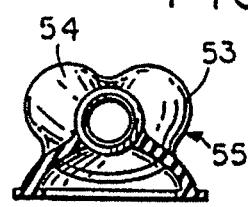
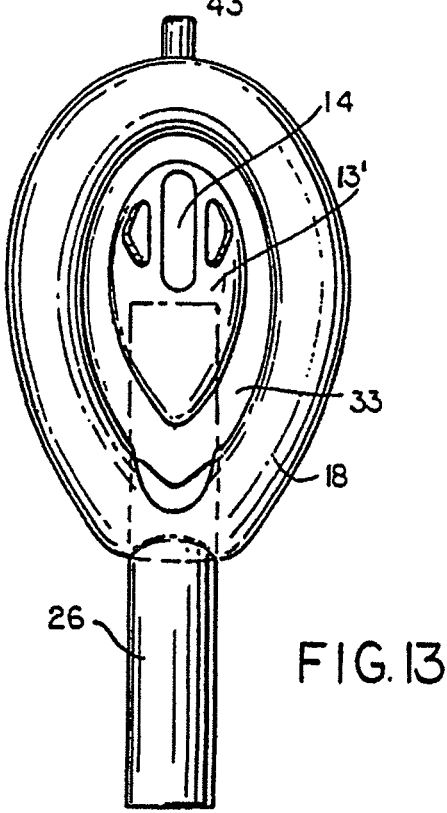

GASTRO-LARYNGEAL MASK

CROSS-REFERENCE TO RELATED APPLICATIONS

This application is a divisional of and claims priority under 35 U.S.C. §120 to U.S. patent application Ser. No. 11/958,946, filed Dec. 18, 2007, entitled Gastro-Laryngeal Mask, the entire contents of which are incorporated herein by reference, which is a continuation of U.S. patent application Ser. No. 09/803,452, now U.S. Pat. No. RE39938, filed on Mar. 8, 2001, entitled Gastro-Laryngeal Mask, the entire contents of which are incorporated herein by reference, which is a reissue of patent application Ser. No. 08/921,169, now U.S. Pat. No. 5,878,745, filed on Aug. 29, 1997, entitled Gastro-Laryngeal Mask, the entire contents of which are incorporated herein by reference, which is a continuation of and claims priority under 35 U.S.C. §120 to U.S. patent application Ser. No. 08/609,521, filed on Mar. 1, 1996, entitled Gastro-Laryngeal Mask, now abandoned.

BACKGROUND OF THE INVENTION

This invention relates to a laryngeal-mask airway (LMA) device, which is an artificial airway device designed to facilitate lung ventilation in an unconscious patient by forming a low-pressure seal around the laryngeal inlet. An inflatable-ring seal surrounds an appropriately shaped mask which fits into the lower pharynx and is attached to a tube which emerges from the mouth, as for connection to medical gas-supply tubing.

More particularly, the invention relates to a variety of laryngeal masks, known as gastro-laryngeal masks (GLM), wherein provision is made for airway assurance to the patient who is at risk from vomiting or regurgitation of stomach contents while unconscious. U.S. Pat. No. 5,241,956 deals with this problem by providing an evacuation tube which is open through the center of the inflatable seal of the laryngeal mask, thus utilizing the distal end of the inflatable ring as an inflatable-cuff formation which establishes peripherally sealed engagement to the upper sphinctral region of the oesophagus and centrally supports the distal end of the evacuation tube. In addition, said U.S. Pat. No. 5,241,956 discloses a further inflatable cuff carried by the laryngeal mask and by the evacuation tube, for referencing inflation against the back wall of the pharynx, thus making it possible to establish the laryngeal-inlet seal with reduced inflation pressure, as compared with prior structures not having such an additional inflatable cuff.

U.S. Pat. No. 5,305,743 discloses moulding techniques for manufacture of a variety of laryngeal masks, including a gastro-laryngeal mask, wherein an inflatable back cushion provides such referencing inflation against the back wall of the pharynx as to widely distribute the back-wall reference, over substantially the full area of the laryngeal mask. Such a back-cushion construction has been found to be mechanically simple and highly effective, and U.S. Pat. No. 5,355,879 discloses such a back cushion for each of several representative laryngeal-mask constructions.

In practice, although a gastro-laryngeal-mask as described in said U.S. Pat. No. 5,355,879 works well, it has the disadvantage that the gastric evacuation channel needs to be sufficiently stiff to prevent its collapse under the influence of the increased pressure within the back-cushion cuff, when it is inflated in the pharynx. A suitably stiff tube is readily provided, but the whole device is then more difficult to insert into the patient's throat, since insertion involves flexing the device around the angle at the back of the tongue. Provision of a pre-curved airway tube facilitates passage around the back of the tongue, but the advancing distal tip end of the device is then more likely to collide with the glottis (or entrance to the larynx), and indeed it may block the larynx by so doing, with consequent danger to the patient.

BRIEF STATEMENT OF THE INVENTION

It is an object of the invention to provide an improved gastro-laryngeal mask. A specific object is to meet the above object with a construction that specifically avoids problems or difficulties with constructions of said U.S. patents.

Another specific object is to provide for ready compression and flexure of a gastric passage within a back-cushioned or cuffed gastro-laryngeal mask, when the mask is in deflated condition for insertion into the patient's throat.

Furthermore, for the deflated condition of the mask, i.e., in readiness for insertion into the patient's throat, it is an object to enable formation of a flattened flexible leading distal-end edge to self-adapt to and resiliently ride the outer limit of curvature of the patient's airway, throughout the insertional course of the deflated mask and into its locating engagement with the hypopharynx.

It is a further specific object, in conjunction with the foregoing specific objects, to provide for assurance of full patency of the gastric passage within the mask, when the mask has been inflated.

These objects are realized in the present invention by utilizing two structural mechanisms, both of which are operative when the device is inflated; one of these mechanisms prevents lateral compression of the wall of the gastric tube, while the other of these mechanisms prevents antero-posterior compression of the wall of the gastric tube; the result is to assure a substantially circular section within relatively soft portions of the evacuation passage, as long as the device is inflated and in installed position.

In a preferred embodiment of the invention, an artificial airway device to facilitate a patient's lung ventilation comprises an airway tube, an evacuation tube, and a laryngeal mask at one end of both tubes. The mask is of generally elliptical configuration and comprises a body or backplate of relatively stiffly compliant nature, and an inflatable annular cuff or ring of relatively softly compliant nature is connected to and surrounds the body or backplate. When inflated, the annular cuff adapts to and seals around the laryngeal inlet, and an inflatable cushion on the exterior of the inflated annulus bears against the back wall of the pharynx, to thereby forwardly load the inflated annulus into sealed relation with the laryngeal inlet, with the backplate dividing the mask between a laryngeal-chamber side and a pharyngeal-chamber side. The relatively stiff backplate is formed for connection to the airway tube for exclusive communication to the larynx through an opening in the backplate; and the backplate is also configured to guide and support a relatively soft flexible evacuation tube within the pharyngeal-chamber side, from a distally open end for reception of gastric products, to a proximal end for connection to an externally discharging evacuation tube.

It is a feature of the invention that along an aligning path for the flexible evacuation tube within the pharyngeal-chamber side of the mask, a first significant angular fraction of the periphery of the flexible tube is bonded to a stabilizing portion of the backplate, and that a second angular fraction of the periphery of the flexible tube is continuously bonded to the inner surface of the flexible back cushion, such that generally opposite unbonded further angular regions exist between the bonded regions. These unbonded further regions are provided with external stiffening ribs at a succession of axial intervals, to reinforce the unbonded regions against lateral compression when the back cushion and the inflatable ring are under inflation pressure. In this way, inflation of the annular laryngeal-inlet sealing ring and of the flexible back cushion will assure a maximally open evacuation passage within the mask in inflated condition, essentially without antero-posterior or lateral compression of the passage. And it is further assured that upon deflation of the mask, evacuation-passage compression will be essentially in the sense of achieving a squeezing and somewhat flattening deformation of the discharge passage against the formed back-plate area of evacuation-passage support; such flattening is maximal at the oesophageal end of the discharge passage, so that, when correctly deflated, the device forms a wedge shape for correct insertion.

BRIEF DESCRIPTION OF THE DRAWINGS

The invention will be illustratively described in detail for a presently preferred embodiment, and for certain other embodiments, all in conjunction with the accompanying drawings, in which:

FIG. 1 is a simplified view, generally in side elevation, for the presently preferred embodiment of an artificial airway device, having at its distal end a laryngeal mask with a gastric-drainage feature of the invention, the same being shown in position for use in a patient;

FIG. 2 is a fragmentary plan view, to an enlarged scale showing the back or pharynx-facing side of the mask of FIG. 1;

FIG. 3 is a plan view to the scale of FIG. 2, showing a softly compliant moulded inflatable component of the mask, as seen from the aspect of FIG. 2;

FIG. 4 is a plan view to the scale of FIG. 2, showing a relatively stiffly compliant rigidising or reinforcing back-plate component of the mask, as seen from the aspect of FIG. 2;

FIG. 5 is a longitudinal section of the softly compliant component of FIG. 3, to the scale of FIGS. 2 to 4 and taken generally in the vertical plane 5-5 of substantial symmetry, but prior to an inside-out deformation step, to create the appearance of FIG. 3;

FIG. 5A is a section, taken at 5A-5A in FIG. 5;

FIG. 6 is another view in longitudinal section, to the scale of FIGS. 2 to 5 and in the vertical plane 5-5 of FIG. 3, showing the relatively stiff component of FIG. 4 in assembled relation to the softly compliant component of FIG. 3;

FIG. 7 is an end view, being a proximally directed view, of the distal end of the rigidising component of FIG. 4;

FIG. 8 is a simplified cross-sectional view of the inflated mask of FIG. 2, taken at 8-8 in FIG. 2;

FIG. 9 is a simplified cross-sectional view of the deflated mask of FIG. 2, taken at 8-8 in FIG. 2;

FIG. 10 is a view similar to FIG. 2, to show a first modification;

FIG. 11 is a view similar to FIG. 4, to show the back-plate component in the modification of FIG. 10;

FIG. 12 is a sectional view, taken at 12-12 in FIG. 11; and

FIG. 13 is a plan view to the scale of FIG. 2 to illustrate an intermediate product which is a modification of that shown in FIGS. 5 and 6.

DETAILED DESCRIPTION

Referring first to the preferred embodiments of FIGS. 1 to 9, the invention is shown in application to an airway system comprising a laryngeal-mask unit 10 and its airway tube 11, installed through the mouth 12 of a patient. The mask unit 10 may be generally as described in any of the above-identified U.S. patents and therefore need not now be described in detail. It suffices to say that mask unit 10 comprises a relatively stiff body or backing-plate member, generally indicated at 13, and an apertured relatively thin body-membrane portion or panel 13' having an aperture or lumen 14 through which the airway tube 11 can establish a free externally accessible ventilation passage, via the patient's mouth 12 and throat 15, and past the epiglottis 16 to the larynx 17. The body member 13 of mask 10 may be described as generally dome-shaped, with its concave side terminating in a generally elliptical footing, and facing the laryngeal inlet; and its convex side faces the backwall of the pharynx. Body 13 is suitably of an elastomer such as silicone rubber and relatively stiff; and body member 13 is surrounded by an inflatable ring 18 which is generally elliptical and which is circumferentially united to body member 13 in essentially a single plane. The inflatable ring 18 may also be of silicone rubber, although preferably relatively soft and flexible compared to body member 13. An externally accessible tube 19 is the means of supplying air to the inflatable ring 18 and of extracting air from (and therefore collapsing) ring 18 for purposes of insertion in or removal from the patient; check-valve means 21 in tube 19 will be understood to hold a given inflation or to hold a given deflation of ring 18.

In the installed position of FIG. 1, the projecting but blunted distal end 27 of ring 18 is shaped to conform with the base of the hypopharynx where it has established limited entry into the upper sphinctral region of the oesophagus 24. The back side of body member 13 is covered by a thin flexible panel 25 (FIG. 2) which is peripherally bonded to the inflatable ring 18 (FIG. 1) and in sealed engagement at peripheral line 25' around the entrance of tubes 11 and 23 to the mask structure to define an inflatable back cushion which assures referencing to the back wall of the pharynx and thus is able to load the mask unit forward for enhanced effectiveness of inflated-ring sealing engagement to the laryngeal inlet. The inflated ring, thus-engaged to the laryngeal inlet, orients the distal-end of the airway tube 11 at an acute angle to the general plane of ring 18 and in substantial alignment with the axis of the laryngeal inlet, for direct airway communication only with the larynx 17.

The laryngeal-mask unit 10 is of the GLM variety in which an evacuation tube 23 (FIG. 2) serves for extraction and external removal of gastric-discharge products from the oesophagus. Tube 23 follows the general course of the airway tube 11, with sealed entry alongside airway tube 11, beneath the back-cushion panel 25, and with passage through the interior of ring 18, near the distal end of the mask; in FIG. 3, the distally open end of the evacuation tube 23 is defined by a re-entrant tubular conduit formation 26 integrally formed with the relatively soft material of ring 18. As explained in U.S. Pat. No. 5,241,956, inflation-air supply to the back cushion may be the same (19) as for ring 18, or separate inflating means (not shown) may be provided for these separate inflatable means.

More specifically, for the particular construction shown, the relatively softly compliant flexible components may be integrally formed in a single moulding operation, in which the moulded intermediate product is an inside-out version of what will become the finished more flexible part of the finished mask unit 10. The moulded intermediate product may thus have the appearance shown in FIG. 5, following the technique described in U.S. Pat. No. 5,305,743, to which reference is made for detailed description. It suffices here to identify the inflation-air inlet formation 28, directed inwardly on a central axis 29 which also includes the outwardly directed distal-end formation of the evacuation tube 26; the central axis 29 may also be understood as identifying the equator plane (perpendicular to the drawing of FIG. 5) which applies to the inflatable annular ring 18, after evacuation tube 26 has been swung upward (counterclockwise), in the sense suggested by arrow 30, and generally for 180.degree. of rotation about an axis 31, which (axis 31) is normal to the plane of the drawing of FIG. 5. This 180.degree. rotation tucks tube 26 into the flange relatively large edge 32 of the open skirt of the moulded intermediate product of FIG. 5 and makes it a simple matter to turn the remainder of the skirt inside-out, thus defining ring 18, with the edge flange 32 seated on a ledge 33 of the upper dome-shaped feature (body-membrane portion or liner 13') of the moulded intermediate product.

In the preferred form shown, the mask body member 13 (FIGS. 4 and 7) is a separately moulded component of relatively stiff nature as compared to the moulded intermediate product of FIG. 5. Stiffness vs. softness will be understood to be relative terms and not necessarily to imply that these components are formed from different materials.

In FIG. 4, the body component 13 is seen to comprise an apertured panel which is essentially a moulded dome or bowl 34 having a concave inner surface which conforms to the convex moulded contour of the dome shape 35 of the relatively soft (i.e., thin-walled) component of FIG. 5, these components being shown in FIG. 6 in assembled relation. Relative stiffness (thickness) in the bowl or dome 34 of FIG. 4 is generally in the range 2 to 5 mm, with gradually reducing thickness for greater flexibility in approach to the lower or distal end. The bowl or dome 34 has a peripheral edge which terminates in a single plane, for adhesively bonded seating to the ledge 33 of the relatively soft component of FIG. 5, after making the inside-out inversion.

The stiffness of body member 13 is greatest in the region of proximal-end seating to ledge 33, above which an inlet-air formation 36 is oriented on an axis 37 which is not only inclined at an acute angle .alpha. to the plane of seating to ledge 33, but is also laterally offset from the central longitudinal plane of symmetry of the mask, denoted 5-5 in FIG. 3. Relative stiffness of body member 13 is also enhanced (i) by the fact that its distal half features a slot 38 of width less than the diameter of the re-entrant distal-end tube 26, (ii) by the fact that the re-entrant tube 26 is adhesively retained in cradled support by and between confronting edges of slot 38, and (iii) by the fact that the distal end of evacuation tube 23 is preferably preformed (as seen in FIG. 2) with a quarter-turn helical advance to track the course of slot 38 in the upper or proximal half of body member 13. The evacuation tube 23 is preferably relatively stiff, e.g., stiffness (thickness) in the order of magnitude of the material at the upper (proximal) half of body member 13, and is seen in FIG. 2 to have telescoping fit to the proximally directed upper end of re-entrant tube 26; this is an adhesively sealed fit.

Stated in other words and in explanation of the distal and proximal halves of the body member 13 and the relation of these halves to the relatively thin material and distal-half extent of re-entrant tubular conduit 26, said tubular conduit may be said to extend proximally to approximately 50 percent of the longitudinal extent of the inflatable ring 18; alternatively, said tubular conduit 26 may be said to extend proximally to at least substantially 50 percent of the longitudinal extent of the inflatable ring 18, consistent with the drawings of FIGS. 2, 3, and 6. Furthermore, as seen in FIG. 4, the distal half of backing-plate member 13 is essentially straight, thus determining a straight proximal direction of tubular conduit 26 for substantially the distal half of the longitudinal extent of the mask.

As also seen in FIG. 2, the back-cushion panel 25 covers a substantial part of the posterior surface of the mask, being peripherally sealed around the generally elliptical course of inflatable ring 18, and also being centrally adhered to the re-entrant tube 26 for substantially the entire length of tube 26, as suggested by cross-hatching 39. Finally, to assure integrity of the inflatable ring 18, the re-entrant tube 26 is adhesively sealed to the adjacent edges of tube-26 local passage through ring 18 at the distal location designated 40 in FIG. 3; for purposes of avoiding undue complexity in the drawings, this adhesively sealed region is not shown but will be understood to be along the line of tube-26 intercept with locally adjacent walls of inflatable ring 18. In FIG. 5, this intercept line is accounted for by a local cut-out 40' at the distal end of the skirt of the intermediate product of FIG. 5.

The simplified sectional diagram of FIG. 8 illustrates the functional cooperation of described component parts and features of the described gastro-laryngeal mask construction, in inflated condition, to account for diametrically opposite section cuts through right and left halves of the inflatable ring 18, spaced by sealed fit of body member 13 to the inner profile of ring 18. The back-cushion panel 25, being centrally adhered at 39 to the upper central region of re-entrant tube 26, provides a lifting force which is in the direction to hold open the evacuation tube and, therefore, not to collapse tube 26 when the back cushion is inflated; without this force, in opposition to a retaining force attributable to adhesive connection to body member 13 (along edges of slot 38), there would be no tendency to hold a softly compliant tube 26 against collapse, in that the cushion panel would outwardly expand itself to a bowed shape 25' suggested by phantom outline in FIGS. 6 and 8.

Preferably, the effective arcuate extent of adhesive connection 39 is in the range 45.degree. to 90.degree. about the central axis of tube 26, as seen in FIG. 8. Preferably also, the adhesive connection of tube 26 along the straight edges of the distal half of slot 38 accounts for a corresponding range of support of tube 26 against collapse in the circumstance of back-cushion inflation. In other words, inflation of the ring 18 and back cushion 25 will assure developed vertical forces to hold the evacuation passage of re-entrant tube 26 in substantially open condition, but the transversely opposed arcuate regions (each of approximately 90.degree. arcuate extent) between these adhesively connected regions are vulnerable to compressionally inward bowing, thus reducing the sectional area of tube 26 while the mask is inflated. The invention resolves this vulnerability by providing axially spaced stiffening ribs or ridges 42 as integral formations of the re-entrant tube 26, in the initially moulded intermediate product of FIG. 5. As shown, there are three mutually opposed pairs of ridges 42, at axial spacings which are in the order of the unstressed bore diameter of tube 26. For the indicated silicone-rubber material of the product of FIG. 5, the incremental local thickness at ridges 42 is suitably twice or three times the otherwise uniformly thin moulded product of FIG. 5, as seen in FIG. 5A.

In FIG. 8, a section taken near the location of tube 26 connection to the more stiffly compliant evacuation tube 23, the inflated condition of the GLM mask of the invention is seen to have an overall "height" dimensions $H.sub.1$, meaning front-to-back (i.e., laryngeal inlet-to-pharynx back wall). When the mask is deflated, this dimension $H.sub.1$ is seen to be reduced by approximately 50 percent, as shown at $H.sub.2$ in FIG. 9 for the deflated condition of the same mask. When deflated, as has been pointed out in U.S. Pat. No. 5,297,547, the ring 18 collapses into flattened double walls (marked 18') which are upwardly dished; and although deflation does little to compress tube 26 other than at the region 39' of adhesion to the back-cushion panel 25, the overall deflated extent H.sub.2 is essentially unchanged from the dimension H.sub.2 which applies for collapse of ring 18. On the other hand, at the distal end of the mask, the collapse of ring 18 is operative upon the formed distal-end opening 43 of tube 26 to somewhat flatten the opening 43, into a generally shovel-shaped distal lip feature which merges smoothly into the adjacent upwardly dished double-wall. shape 18' shown in the longitudinal midsection of FIG. 9.

It will be appreciated that the GLM device described thus far has an airway tube 11 that is of larger diameter than the evacuation tube 23; in this circumstance, the airway tube 11 is large enough to accommodate guided insertion of an endotracheal tube. The tubes 11, 23 enter the described laryngeal mask 10 in side-by-side relation and are preferably adhesively secured to each other in this side-by-side relation, and along their full longitudinal extent, in order to provide a measure of torsional resistance against twisting, thereby aiding a medically qualified person in quickly and correctly installing a fully deflated GLM in a patient, with assurance that, upon inflation of ring 18 and the back-cushion panel 25, an exclusive and sealed airway connection will be established to the laryngeal inlet, via lumen 14 and from the airway tube 11; concurrently, a similarly exclusive evacuation connection is established to the upper sphinctral region of the oesophagus, via the distal-end opening 43 of tube 26, through the evacuation tube 23, and to suitable waste-collection means (not shown) external to the patient.

More specifically as to insertion of the fully deflated GLM device in a patient, it will be understood that a range of GLM sizes is available from which to select a sufficiently correct size for the patient. Deflation is accomplished via external means (not shown) and via check-valve means 21 to hold the deflated condition wherein the dome shape of body member 13 rises from within the dished peripheral lip 18' of the collapsed ring 18. A skilled operator is quickly able to develop the desired appearance of the GLM in its deflated state; but for a uniformly correct deflated shaping, it is recommended to use a forming tool as described in U.S. Pat. No. 5,711,293.

When correctly shaped and in its deflated condition, and at the distal end of the GLM, the opening 43 will have been flattened, and this distal end merges with the peripheral lip 18' of the collapsed ring 18. Noting that the entire distal half of the mask is of relatively soft material, stiffened only by indicated adhesive connection, the distal end projects distally and at its upwardly flared merge with lip 18', for low acute-angle incidence to the posterior arcuate profile of the patient's throat passage. That being the case, a medical technician need only make sure that upon inserting the mask via the patient's mouth and throat, the flattened distal end rides the outer (posterior) arcuate contour of the patient's airway, in that the softly flexible nature of the distally projecting and somewhat flattened distal end will be flexibly self-adapting to local irregularities (if any) in the course of passage into the pharynx; final insertional location is noted by an increase in encountered resistance, upon distal-end engagement of the GLM with the upper sphinctral region of the oesophagus. At this juncture, inflation air supplied via line 19 and retained by check-valve means 21 establishes (i) the described seal of ring 18 to the laryngeal inlet, (ii) back cushion (panel 25) contact with the back wall of the pharynx, and (iii) full opening of the evacuation tube 26 for maximum accommodation of a possible gastric discharge from the oesophagus.

Beyond what has been described, FIG. 10 illustrates at phantom outline 26' that the flexible length of the re-entrant tube 26 may be of even greater length than the approximately half-mask length shown by the solid lines of FIG. 5. In that event, arcuate stiffener ridges as described at 42 will be preferred, as long as lateral support is needed to prevent side-wall collapse of the extended tube 26', in the inflated condition of the mask, i.e., including inflation of back-cushion panel 25.

FIGS. 10 to 12 illustrate another GLM embodiment wherein an airway tube 50 and an evacuation tube 51 are of equal size, adhered (as suggested at 52) to each other in side-by-side relation for torsionally resistant and symmetrically positioned entry into corresponding side-by-side ports 53, 54 of the dome like moulded backing plate or body member 55 of FIGS. 11 and 12. The backing plate 55 may be similar to plate 13 of FIG. 4, except that in FIG. 11 the somewhat helically arcuate conduit path from the inserted distal end of evacuation tube 51 to the point 56 of softly compliant re-entrant tube (26) connection is provided by an integral passage formation 57 of the backing plate 55. At point 56 in FIG. 11, the formation 57 is seen to be in the central vertical plane 58 of symmetry of the bowl or dome-shape of backing plate 55 and in alignment for accepted proximal-end insertional accommodation of a re-entrant tube 26 of thin-walled material to which backing plate 55 is to be assembled, with edges of the straight slot 38' supporting tube 26 in the manner already described. Also integrally formed with backing plate 55 is an inlet-connection counterbore for coupled connection of airway tube 50 to the laryngeally exposed side of the mask. Features in FIG. 10, such as the back-cushion panel 25, the inflatable ring 18, and the adhesively bonded connection 39 of panel 25 to tube 26 are all as previously described.

It will be understood that the inside-out technique described in connection with FIGS. 5 and 6 for initially moulding and then inverting the skirt of the moulded product, is but one illustration of a way to create the mask and its inflatable ring, in which case the flexible drainage conduit does not get inverted. That being the case, the reinforcement ribs 42 are initially formed portions of the outer surface of the moulded product. On the other hand, another technique for forming the mask with its inflatable ring, involves moulding the mask bowl integrally with an elliptically configured product as shown in FIG. 13, wherein completion of inflatable-ring (18) integrity requires only an adhesively bonded completion of the ring peripherally around the inner substantially elliptical profile, where backing-plate (13) connection is also adhesively secured. In that case, the drainage tube 26 is integrally-moulded with the non-invertible ring (18), so that an inversion of tube 26 is necessary, to have it project re-entrantly, in the proximal direction, and the moulded product which is to become inflatable ring 18 must be cut away as at 40, to permit inverted tube 26 to "pass through" the inflatable ring, in order to develop a relationship which is suggested by FIG. 5. Of course, if tube 26 is to be inverted, the reinforcement ribs 42 are preferably integrally formed as radially inward rib reinforcements or discontinuities in the moulded bore of tube 26. Inversion of tube 26 places these rib reinforcements on the outer surface of tube 26, so that the bore of tube 26 is inherently smooth.

What is claimed is:
1. A method of making a device including:
(A) providing an inflatable mask comprising a relatively stiff component and a relatively soft compliant flexible component, the mask being insertable, at least when deflated, through a mouth of a patient to an inserted location within the patient, the inserted location being near a laryngeal inlet of the patient;

(B) providing an airway tube coupled to the mask, the airway tube extending from a proximal end located outside of the patient's mouth through an interdental gap to the mask when the mask is at the inserted location, the interdental gap being a space between the patient's lower teeth and the patient's upper teeth;

(C) providing an evacuation tube for communication with an esophageal inlet of the patient, the evacuation tube being coupled to the mask, the evacuation tube extending from a proximal end located outside of the patient's mouth through the interdental gap to the mask when the mask is at the inserted location; and integrally forming the relatively soft compliant flexible component of the mask in a single moulding operation;

wherein integrally forming the relatively soft compliant flexible component of the mask comprises integrally forming an inflation-air inlet formation, an outwardly directed distal-end tube and an open skirt.

2. A method of making a device according to claim 1, further including a step of rotating the outwardly directed distal-end with respect to the open skirt and tucking the integrally formed distal-end tube into a flange of the open skirt.

3. A method of making a device according to claim 2, further including a step of turning a portion of the skirt inside-out, thus defining a ring.

4. A method of making a device according to claim 3, further comprising the step of adhesively bonding the relatively stiff component to the relatively soft component after the skirt has been turned inside-out.

5. A method of making a device according to claim 4, wherein the relatively stiff component comprises a back-cushion panel, and the back-cushion panel is centrally adhered to the inwardly directed distal-end tube of the relatively soft component.

6. A method of making a device according to claim 4, wherein the edges of the inwardly directed distal-end tube are adhesively sealed to the locally adjacent walls of the ring.

7. A method of making a device according to claim 4, further comprising adhesively sealing the evacuation tube to the inwardly directed distal-end tube after the relatively stiff component has been adhesively bonded to the relatively soft component.

8. A method of making a device according to claim 1, wherein integrally forming the mask comprises integrally forming axially spaced stiffening ribs or ridges located on the outwardly directed distal-end tube.

9. A method of making a device according to claim 8, wherein the axially spaced stiffening ribs or ridges are integrally formed on the inner surface of the outwardly directed distal-end tube so that after the outwardly directed distal-end tube is tucked into the flange of the open skirt the axially spaced stiffening ribs or ridges are located on the outer surface of the inwardly directed distal-end tube.

* * * * *